(12) United States Patent
Renes et al.

(10) Patent No.: US 8,101,223 B2
(45) Date of Patent: Jan. 24, 2012

(54) FLAVOUR MODULATING SUBSTANCES

(75) Inventors: Harry Renes, Lelystad (NL); Chris Winkel, Bussum (NL); Eric Kohlen, Leusden (NL); Jan Visser, Huizen (NL); Emelie Verhoek, Zeewolde (NL)

(73) Assignee: Givaudan Nederland Services B.V., Naarden (NL)

( * ) Notice: Subject to any disclaimer, the term of this patent is extended or adjusted under 35 U.S.C. 154(b) by 780 days.

(21) Appl. No.: 12/089,043

(22) PCT Filed: Oct. 5, 2006

(86) PCT No.: PCT/NL2006/050243
§ 371 (c)(1),
(2), (4) Date: Apr. 2, 2008

(87) PCT Pub. No.: WO2007/040399
PCT Pub. Date: Apr. 12, 2007

(65) Prior Publication Data
US 2008/0268122 A1 Oct. 30, 2008

(30) Foreign Application Priority Data
Oct. 6, 2005 (EP) .................................... 05109303

(51) Int. Cl.
*A23L 1/22* (2006.01)
(52) U.S. Cl. ........................................ 426/534; 426/650
(58) Field of Classification Search .................. 426/533, 426/534, 535, 536, 537, 538, 650
See application file for complete search history.

(56) References Cited

U.S. PATENT DOCUMENTS

| | | | |
|---|---|---|---|
| 4,420,432 A | 12/1983 | Chibata et al. | |
| 4,698,230 A * | 10/1987 | Willard | 426/533 |
| 4,956,489 A | 9/1990 | Auriol et al. | |
| 5,780,090 A | 7/1998 | Frerot et al. | |
| 2002/0187241 A1* | 12/2002 | Young et al. | 426/594 |

FOREIGN PATENT DOCUMENTS

| | | |
|---|---|---|
| EP | 1 356 744 | 8/2003 |
| EP | 1 344 459 | 9/2003 |
| JP | 11 199444 | 7/1999 |
| WO | WO 2004/075663 | 9/2004 |
| WO | WO 2005/102071 | 11/2005 |

* cited by examiner

*Primary Examiner* — Leslie Wong
(74) *Attorney, Agent, or Firm* — Curatolo Sidoti Co., LPA; Joseph G. Curatolo; Salvatore A. Sidoti

(57) ABSTRACT

The present invention in a first aspect relates to flavor modulation in foodstuffs, beverages, orally administered pharmaceuticals, tobacco products and oral care products, using a flavor modulating substance selected from the group of substances represented by formula, edible salts thereof and edible esters thereof: formula wherein $R^1$ and/or $R^2$ represent the residue of primary amines, more particularly the residues of primary amines selected from amino acids, peptides, purines and pyrimidines, aralkylamines and certain branched or straight chain, hydrophilically substituted alkylamines. It has been found that these substances are capable imparting highly desirable taste attributes in the products they are incorporated in. In addition said flavor modulating substances are advantageously applied in flavor compositions, foodstuffs, orally administered pharmaceuticals, tobacco products and oral care products.

11 Claims, No Drawings

FLAVOUR MODULATING SUBSTANCES

The present application is a United States National Stage of International Patent Application No. PCT/NL2006/050243, filed on Oct. 5, 2006, which claims the benefit of (Paris Convention priority) European Patent Application No. 05109303.7, filed on Oct. 6, 2005. The entire disclosures of International Application No. PCT/NL2006/050243 and European Patent Application No. 05109303.7 are incorporated herein by reference.

FIELD OF THE INVENTION

The present invention relates to the field of improving the flavour of foodstuffs, beverages, orally administered pharmaceuticals, tobacco products and oral care products. More particularly, the present invention provides flavour compositions that can be used to confer a fuller and richer taste to foodstuffs, beverages, orally administered pharmaceuticals, tobacco products and oral care products. The flavour compositions according to the invention are characterised by the presence of one or more flavour modulating substances that are capable of improving and complementing the impact of other flavour imparting substances.

The present invention also encompasses the use of the aforementioned flavour modulating substances for improving the taste of foodstuffs, beverages, orally administered pharmaceuticals, tobacco products and oral care products, as well as to foodstuffs, beverages, orally administered pharmaceuticals, tobacco products and oral care products containing these substances.

BACKGROUND OF THE INVENTION

The flavour of foodstuffs and beverages consists of two parts: the aroma and the taste. In general what is perceived through the olfactory epithelium in the nasal cavity is referred to as 'aroma', whereas the term 'taste' is generally used to describe the sensory impact that is perceived via the mouth, especially the tongue. The flavour sensation experienced upon consumption, especially the taste, provides the final analysis of food prior to ingestion thereof. Visual and olfactory (smell) signals already give a first indication but only after intake of the food into the mouth the final decision is made either to ingest or to reject the food. Sweet taste is usually a signal that the food is safe (appetising) leading to ingestion of the food. The 'reactions' to salt and umami are really dependent on the strength of the signal. Bitter and sour are usually experienced as repulsive taste sensations that can lead to rejection. Temperature is another measure by which the food is judged just as well as aching sensations like capsaicin (hot pepper) and certain chemicals (like carbon dioxide).

In short, this means that taste is a very important and very complex system. Until recently most flavour research was focused towards aroma. Especially the last years a series of publications relating to molecules with a (positive) contribution to the taste of foodstuffs has emerged.

Such research has been stimulated significantly by the fact that quite some receptors which are involved in the different taste sensations have been characterized by now (B. Lindemann; Nature 413, 219 (2001)).

Another interesting aspect of taste is that it can have an impact on aroma. It was reported that people having artificially sweetened water in their mouth were significantly more sensitive to the smell of benzaldehyde than people having plain water in their mouth (P. Dalton et al, Nature Neurosci. 3, 431-432 (2000)).

Several screening systems have been described that make it possible to screen, in a short time, large series of molecules for their (modulating) effect on taste response (cf. WO04055048, GB2396414, WO0177292 and US2004/0072254).

Most research on taste modulation so far has been devoted to taste enhancement in savoury products. Several, mainly Japanese, publications describe umami molecules, i.e. alternatives to mono sodium glutamate (MSG) (H Suzuki et al, J Agric Food Chem 50, 313-318 (2002); K Shima et al, J Agric Food Chem 46, 1465-1468 (1998); Y Ueda et al, Biosc Biotech Biochem 61 1977 (1997)).

In EP 1291342, a 'general taste enhancer' is disclosed that was reported to be suitable for enhancing sweetness as well.

Alpha keto acids are reported to give body and mouthfeel to foodstuffs they are added to (U.S. Pat. No. 6,287,620).

Chlorogenic acids are claimed to enhance sweetness and to reduce bitterness (WO02100192).

WO 97/04667 relates to certain tripeptides as well as to substances that include an N-lactoyl radical and a residue of one of the common amino acids. These so-called N-lactoyl-X type substances, wherein X represents the amino acid residue, are deemed to have the following structural feature in common, R' representing the side chain of one of the 20 proteogenic amino acids:

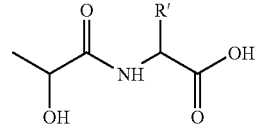

The tripeptides and N-lactoyl-X type substances according to WO 97/04667 were found to constitute useful flavouring ingredients. According to this document these flavouring ingredients are capable of improving the oral perception or mouthfeel of products to which they are added and producing organoleptic effects of the type of that which can be obtained using MSG.

WO04/075663 concerns the use of derivatives of dicarboxylic acids and amino acids as flavouring ingredients, more particularly as mouthfeel and/or umami agents and/or as MSG partial or total replacers. WO 04/075663 teaches the following common structure of these derivatives:

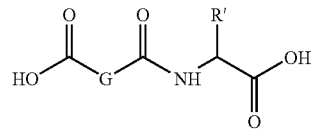

wherein G represents a linear $C_1$-$C_6$ alkyl group, in particular $CH_2$, $CH_2CH_2$ or $CH_2CH_2CH_2$, or a HC=CH group, and R' represents the side chain of one of the 20 proteogenic amino acids.

There is still a need for new so-called flavour modulating substances that provide a positive contribution to the flavour, especially the taste, of foodstuffs, beverages, orally administered pharmaceuticals, tobacco products and oral care products they are incorporated in. One objective of the present invention is to provide such substances and compositions comprising them.

SUMMARY OF THE INVENTION

The present inventors have surprisingly found that substances according to formula (I), wherein R1 and/or R2 represent the residue of primary amines, more particularly the residues of primary amines selected from amino acids, peptides, purines and pyrimidines, aralkylamines and certain branched or straight chain, hydrophilically substituted alkylamines, as well as edible salts and esters of said substances, can be used advantageously to improve the flavour of foodstuffs, beverages, orally administered pharmaceuticals, tobacco products and oral care products:

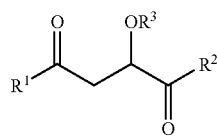

(I)

Several derivatives of malic acid and amino acids have been described before. JP 11199444 and U.S. Pat. No. 4,956,489 both disclose derivatives of malic acid and tyrosine. Both of these documents relate to cosmetic applications of said substances. JP 11199444 also discloses compositions comprising the malic acid tyrosine derivative and monocyclic terpenes, such as menthol or limonene, which are used as a prophylactic treatment of grey hair.

A derivative of malic acid and phenylalanine has been disclosed in a publication by J. Gouesnard (Bulletin de la Societe Chimique de France 1, 88-94 (1989)). Kasai et al. described two new acidic acylarginine derivatives, among which a derivative of malic acid and arginine, which was isolated from tubers of *Smilax china* and seeds of *Vicia faba* (Phytochemistry (Elsevier) 22 (1), 147-149 (1983)). In these publications no reference whatsoever is made to organoleptic properties of these derivatives. In U.S. Pat. No. 4,420,432 crystalline salts of L-amino acids with L-malic acid are disclosed. This document however does not disclose any derivatives of amino acids and malic acids, i.e. wherein the said moieties are attached through a covalent bond.

The inventors have found that the aforementioned flavour modulating substances can advantageously be employed to impart desirable taste attributes in a wide variety of applications and products, especially food, beverages, orally administered pharmaceuticals, tobacco products and oral care products. In addition, the present flavour modulating substances are capable of modifying the taste and/or aroma impact of other flavour ingredients contained within these same products, thereby improving the overall flavour quality of these products.

The present invention thus relates to the aforementioned flavour modulating substances and to flavour compositions, foodstuffs, beverages, orally administered pharmaceuticals, tobacco products and oral care products comprising one or more of these flavour modulating substances. Other aspects of the present invention relate to the use of said flavour modulating substances for improving the flavour of foodstuffs, beverages, orally administered pharmaceuticals, tobacco products and oral care products.

DETAILED DESCRIPTION OF THE INVENTION

Flavour modulating substances that can be used in accordance with the present invention in flavour compositions, foodstuffs, beverages, orally administered pharmaceuticals, tobacco products and oral care products are selected from the group of substances represented by formula (I), edible esters thereof and edible salts thereof:

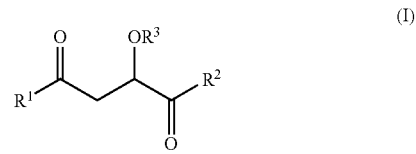

(I)

wherein:
$R^1$ and $R^2$ independently represent:
  a hydroxyl group;
  an amino acid residue;
  the residue of a peptide; or
  a moiety represented by the formula —NH—X, wherein X represents:
   1) $C_1$-$C_4$ alkyl or $C_4$-$C_7$ aralkyl, each substituted with a substituent selected from hydroxyl or $C_1$-$C_3$ alkoxyl, and each optionally further substituted with one or more substituents selected from hydroxyl, oxo, $C_1$-$C_3$ alkoxyl and $C_1$-$C_3$ alkyl;
   2) a purine or pyrimidine radical, each optionally substituted with one or more substituents selected from the group of amino, oxo, methyl and monosaccharide units, said monosaccharide unit optionally being esterified with a mono-, di- or triphosphate group; or
   3) $C_5$-$C_7$ polyhydroxy carboxylic acid or an intramolecular-condensation product thereof; or
   4) $C_5$-$C_7$ polyhydroxy carbonyl or an intramolecular-condensation product thereof;
and wherein $R^3$ represents hydrogen or $C_1$-$C_3$ alkyl;
with the proviso that if one of $R^1$ and $R^2$ represents a hydroxyl group, the other one does not represent a hydroxyl group.

The term "aralkyl" as used herein refers to an aryl group substituted with an alkyl radical, such as a benzyl group, for example. An aralkyl group may optionally be substituted at the alkyl moiety and/or at one or more ring positions with any group known as an aryl or alkyl substituent respectively.

As used herein, the term "amino acid residue", has the meaning common in the art of protein chemistry, i.e. a moiety according to the formula —NH—CHR$^a$—COOH, R$^a$ being the amino acid side chain. Typically, said term can refer to a residue of both a proteogenic and a non-proteogenic amino acid. The group of proteogenic amino acids comprises the 20 amino acids that are abundant in nature as, amongst others, building blocks for the synthesis of proteins and peptides. These 20 amino acids are L-glycine (Gly), L-alanine (Ala), L-valine (Val), L-leucine (Leu), L-isoleucine (Ile), L-prone (Pro), L-serine (Ser), L-threonine (Thr), L-phenylalanine (Phe), L-tyrosine (Tyr), L-tryptophan (Trp), L-lysine (Lys), L-arginine (Arg), L-histidine (His), L-aspartic acid (Asp), L-glutamic acid (Glu), L-asparagine (Asn), L-glutamine (Gln), L-cysteine (Cys) and L-methionine (Met). Suitable examples of non-proteogenic amino acids include ornithine, 2,4-diaminobutyric acid and 2,3-diaminopropionic acid.

As used herein, the term "the residue of a peptide" refers to any polymer of two or more amino acid residues, linked to each other with a peptide bond, i.e. a moiety according to the formula —NH—CHR$^a$—COO—(NH—CHR$^a$—COO)$_n$H, wherein n is at least 1.

As used herein the terms "polyhydroxy carboxylic acid" and "polyhydroxy carbonyl" relate to a carboxylic acid moiety or carbonyl moiety respectively comprising two or more hydroxyl substituents.

The present inventors have found that the above-mentioned flavour modulating substances are very useful flavour ingredients which, particularly in the presence of other flavour imparting substances, are capable of imparting highly appreciated taste sensations to the products in which they are incorporated, specifically "roundness", "fullness", "substance", "continuity", "complexity", "long lasting", "kokumi" and/or "yeasty", "bite", "bitter", and/or, "mature cheese taste". Because of this, the present substances can be employed to improve the flavour, especially taste (including "mouthfeel"), of foodstuffs, beverages, orally administered pharmaceuticals, tobacco product and oral care products.

The flavour modulating substances of the present invention as such are capable of imparting highly desirable taste attributes. In addition, it has been found that the flavour modulating substances according to the invention are capable of complementing and modifying the sensory impact of other, flavour imparting, substances, contained in the aforementioned products, including complementing and modulating sweet taste impact and savoury taste impact.

Throughout this document the term "flavour" is used to describe the sensory impact that is perceived via the mouth, especially the tongue, and the olfactory epithelium in the nasal cavity. The term "complementing and modifying the sensory impact" as used herein refers to the capability of the present compositions or substances to alter the taste and/or aroma impact of other, flavour imparting, substances present within the same product, with the proviso that this change in taste impact is not caused by the flavour contribution of said composition or substance per se, but instead that it mainly results from the combined effect of on the one hand the present flavour modulating composition or substance and on the other hand the other flavour imparting substance(s). The present flavour modulating substances combine the capability of modulating the taste and/or aroma of other, flavour imparting, substances and a taste contribution of their own. The favourable impact of the present flavour modulating substances is believed to be the result of the combination of these two effects.

Because the flavour modulating substances according to the invention are not particularly volatile, they do not produce a strong aroma impact, even though they can affect the aroma impact of other flavour imparting substances. Here the term "aroma" refers to the aspect of flavour that is perceived through the olfactory epithelium. Because of the low volatility of the present flavour modulating substances it is believed that the advantageous properties of these substances are somehow associated with the impact that these substances have on the sensory receptors located within the mouth.

According to a preferred embodiment, the present flavour modulating substances are selected from the group of substances represented by formula (I), edible esters thereof and edible salts thereof as defined herein before, wherein $R^1$ and $R^2$ independently represent a hydroxyl group or an amino acid residue. More preferably R1 and $R^2$ independently represent a hydroxyl group or the residue of any one of the aforementioned 20 proteogenic amino acids, still more preferably the residue of an amino acid selected from Glu, Asp, Ala, Lys, Leu, Gly, Met and Gln.

According to another equally preferred embodiment, the present flavour modulating substances are selected from the group of substances represented by formula (I), edible esters thereof and edible salts thereof as defined herein before, wherein $R^1$ and $R^2$ independently represent a hydroxyl group or the residue of a peptide, wherein said peptide comprises 2-15, more preferably 2-10, still more preferably 2-5, most preferably 2 or 3 amino acid residues. It is particularly preferred that said amino acid residues are selected from the group of 20 proteogenic amino acids. It is even more preferred that the present peptide at least comprises one amino acid residue selected from Glu, Asp, Ala, Lys, Leu, Gly, Met and Gln.

According to a particularly preferred embodiment of the invention, the present flavour modulating substances are selected from the group of substances represented by formula (I), edible esters thereof and edible salts thereof as defined herein before, wherein $R^1$ and $R^2$ independently represent a hydroxyl group or a moiety represented by the formula —NH—X.

According to another equally preferred embodiment, the present flavour modulating substances are selected from the group of substances represented by formula (I), edible esters thereof and edible salts thereof as defined herein before, wherein $R^1$ and $R^2$ independently represent a hydroxyl group or a moiety represented by the formula —NH—X wherein X represents a purine or pyrimidine radical each optionally being substituted with one or more substituents selected from the group of amino, oxo, methyl and monosaccharide units, said monosaccharide unit optionally being esterified with a mono-, di- or triphosphate group. Preferably X represents a purine or pyrimidine radical, each at least substituted with a monosaccharide unit, preferably a ribose unit, which is esterified with a mono-, di- or triphosphate group. More preferably $R^1$ and $R^2$ independently represent a hydroxyl group or the residue of guanosine monophosphate (GMP), adenosine monophosphate (AMP) or cytidine monophosphate (CMP), most preferably a hydroxyl group or the residue of guanosine monophosphate.

According to another equally preferred embodiment, the present flavour modulating substances are selected from the group of substances represented by formula (I), edible esters thereof and edible salts thereof as defined herein before, wherein $R^1$ and $R^2$ independently represent a hydroxyl group or a moiety represented by the formula —NH—X wherein X represents $C_1$-$C_4$ alkyl substituted with at least one hydroxyl group and optionally further substituted with one or more substituents selected from hydroxyl and methyl. More preferably X represents $C_2$-$C_3$ alkyl substituted with one hydroxyl group and optionally 1 or 2 substituents selected from hydroxyl and methyl. Still more preferably in the above mentioned formula (I) $R^1$ and $R^2$ independently represent a hydroxyl group or the residue of ethanolamine, 2-amino-1,3-propanediol, 3-amino-1,2-propanediol, 3-amino-1-propanol, 2-amino-1,3-propanediol, 1-amino-2-propanol, 2-amino-1-propanol, 1-amino-2-methyl-2-propanol or 2-amino-2-methylpropanol, most preferably a hydroxyl group or the residue of ethanolamine.

According to another equally preferred embodiment, the present flavour modulating substances are selected from the group of substances represented by formula (I), edible esters thereof and edible salts thereof as defined herein before, wherein $R^1$ and $R^2$ independently represent a hydroxyl group or a moiety represented by the formula —NH—X wherein X represents $C_7$-$C_9$ aralkyl substituted with one or more substituents selected from hydroxyl, methoxyl and ethoxyl and optionally one or more substituents selected from $C_1$-$C_3$ alkyl. More preferably X represents phenylmethyl or phenylethyl, wherein the phenyl ring is substituted with 1-3 substituents selected from hydroxyl, methoxyl and ethoxyl. Still more preferably in the above mentioned formula (I) $R^1$ and $R^2$ independently represent a hydroxyl group or the residue of tyramine, vanillylamine, 4-hydroxybenzylamine or dopamine, most preferably a hydroxyl group or the residue of tyramine.

According to another equally preferred embodiment, the present flavour modulating substances are selected from the group of substances represented by formula (I), edible esters thereof and edible salts thereof as defined herein before, wherein $R^1$ and $R^2$ independently represent a hydroxyl group or a moiety represented by the formula —NH—X wherein X represents $C_5$-$C_7$ polyhydroxy carbonyl or an intramolecular condensation product thereof, typically a cyclic hemiacetal, more preferably a $C_5$-$C_7$ polyhydroxycarbonyl wherein each of the carbon atoms is substituted, or an intramolecular condensation product thereof. Still more preferably in the above mentioned formula (1) $R^1$ and $R^2$ independently represent a hydroxyl group or the residue of a 2-deoxy-2-amino aldose (aldosamine), even more preferably a hydroxyl group or a hexosamine or pentosamine, still more preferably a hydroxyl group or the residue of glucosamine, galactosamine, mannosamine, xylosamine, lactosamine, ribosamine or arabinosamine, most preferably a hydroxyl group or the residue of glucosamine, galactosamine, mannosamine or an intramolecular-condensation product thereof.

According to another equally preferred embodiment, the present flavour modulating substance is selected from the group of substances represented by formula (I), edible esters thereof and edible salts thereof as defined herein before, wherein $R^1$ and $R^2$ independently represent a hydroxyl group or a moiety represented by the formula —NH—X wherein X represents $C_5$-$C_7$ polyhydroxy carboxylic acid or an intramolecular condensation product thereof, typically a lactone, more preferably a $C_5$-$C_7$ polyhydroxy carboxylic acid wherein each of the carbon atoms is substituted or an intramolecular condensation product thereof. Still more preferably in the above mentioned formula (I) $R^1$ and $R^2$ independently represent a hydroxyl group or the residue of a 2-deoxy-2-amino aldonic acid, even more preferably a hydroxyl group or a 2-deoxy-2-amino hexosaminic acid or pentosaminic acid, still more preferably a hydroxyl group or the residue of glucosaminic acid, galactosaminic acid or mannosaminic acid or an intramolecular condensation product thereof.

In the aforementioned formula (I), $R^3$ preferably represents hydrogen.

As used herein the term 'edible esters thereof' typically encompasses any edible derivative of the present flavour modulating substances and an acid. Typically said acid is an organic acid such as a substituted or non-substituted, linear or branched $C_1$-$C_6$ carboxylic acid, more preferably a $C_1$-$C_4$ carboxylic acid, most preferably a $C_1$-$C_3$ carboxylic acid, or alternatively an inorganic acid such as phosphoric acid. Such esters may be hydrolysed to produce flavour modulating substances according to the present invention during storage, processing and the like (acting as so called precursors). Furthermore, said edible esters comprise derivatives of a first flavour modulating substance represented by formula (I) and a second flavour modulating substance represented by formula (I). Said edible esters furthermore comprise derivatives of a flavour modulating substance represented by formula (I) and a malic acid monomer or polymer.

According to a particularly preferred embodiment the present flavour modulating substances are selected from the group of substances represented by formula (I) as defined herein before and edible salts thereof.

According to a particularly preferred embodiment of the present invention the flavour modulating substances are selected from the group of substances represented by the aforementioned formula (I), edible salts thereof, and edible esters thereof wherein:

R1 represents hydroxyl, R2 represents the residue of an amino acid selected from Glu, Asp, Ala, Lys, Leu, Gly, Met and Gln and R3 represents hydrogen; or R1 represents the residue of an amino acid selected from Glu, Asp, Ala, Lys, Leu, Gly, Met and Gln, R2 represents hydroxyl and R3 represents hydrogen; or R1 represents the residue of an amino acid selected from Glu, Asp, Ala, Lys, Leu, Gly, Met and Gln, R2 represents the residue of an amino acid selected from Glu, Asp, Ala, Lys, Leu, Gly, Met and Gln and R3 represents hydrogen; or R1 represents hydroxyl, R2 represents the residue of GMP and R3 represents hydrogen; or R1 represents the residue of GMP, R2 represents the residue of GMP and R3 represents hydrogen; or R1 represents the residue of GMP, R2 represents hydroxyl and R3 represents hydrogen; or R1 represents hydroxyl, R2 represents the residue of ethanolamine and R3 represents hydrogen; or R1 represents the residue of ethanolamine, R2 represents hydroxyl and R3 represents hydrogen; or R1 represents the residue of ethanolamine, R2 represents the residue of ethanolamine and R3 represents hydrogen; or R1 represents hydroxyl, R2 represents the residue of tyramine and R3 represents hydrogen; or R1 represents the residue of tyramine, R2 represents the residue of tyramine and R3 represents hydrogen; or R1 represents the residue of tyramine, R2 represents hydroxyl and R3 represents hydrogen; or R1 represents hydroxyl, R2 represents the residue of glucosamine and R3 represents hydrogen; or R1 represents the residue of glucosamine, R2 represents hydroxyl and R3 represents hydrogen.

As will be apparent from the above, the compounds used as flavour modulating substances in accordance with this invention exhibit optical isomerism and, depending on the method of preparing said substances and the starting materials, may be isomerically pure or they may be isomeric mixtures. Generally, the compounds will be used as isomeric mixtures, but in some cases the flavour modulating effect may differ between isomers, and therefore one or the other isomer may be preferred.

A first aspect of the invention provides a flavour composition comprising at least 0.1 wt. % of one or more flavouring substances and between 0.001 and 95 wt. % of one or more flavour modulating substances selected from the group of substances represented by formula (I), edible salts thereof and edible esters thereof as defined herein before.

Throughout this document the term "flavouring substance" encompasses any substance that is not represented by formula (I) and that is capable of imparting a detectable flavour impact, especially at a concentration below 0.1 wt. %, more preferably below 0.01 wt. %, as well as sweeteners, including saccharide sweeteners and artificial sweeteners. Typically, the present flavouring substance belongs to one of the chemical classes of alcohols, aldehydes, ketones, esters, ethers, acetates, nitriles, terpene hydrocarbons, nitrogenous or sulphurous heterocyclic compounds and essential oils, and said flavouring substances can be of natural or synthetic origin. Many of these are listed in reference texts such as the book by S. Arctander, Perfume and Flavor Chemicals, 1969, Montclair, N.J., USA, or its more recent versions, or in other works of a similar nature, as well as in the abundant patent literature in the field of flavours.

Preferably, the flavour composition according to the invention contains at least 0.1 wt. % of the flavour modulating substances as defined above. Typically, the amount of the flavour modulating substances does not exceed 90 wt. %, preferably it does not exceed 40 wt. %, even more preferably the flavour composition comprises less than 25 wt % of the flavour modulating substance, most preferably less than 5 wt %.

In a preferred embodiment the flavour composition according to the invention comprises flavouring substances in an amount of at least 0.5 wt. %, preferably at least 1 wt. %, based on the total weight of the composition. Preferably, the amount of flavouring substances does not exceed 95 wt %, more preferably it does not exceed 50 wt %.

Preferably, in the present flavour composition the flavour modulating substances and flavouring substances as defined herein before are employed in a weight ratio of less than 50:1, preferably less than 20:1. In a preferred embodiment said weight ratio is within the range of 1:100 to 10:1, more preferably within the range of 1:50 to 5:1. Most preferably, the flavour modulating substances and flavouring substances are employed in a weight ratio that does not exceed 1:1.

The flavour composition according to the present invention may suitably be prepared in the form of a liquid, a paste or a powder. In a particularly preferred embodiment the flavour composition is a free flowing powder. Typically, the present flavour composition comprises at least one flavour carrier, i.e. a material which does not significantly alter the organoleptic properties of the composition. Said carrier may be liquid or solid. Suitable examples include maltodextrin, modified starch, gum Arabic, ethanol and propylene glycol.

In a preferred embodiment, the present flavouring composition is selected from the group consisting of dairy flavourings, e.g. butter and milk flavourings, fruit flavourings, e.g. citrus and red fruit flavourings, savoury flavourings, e.g. meat and cheese flavourings, and bread flavourings.

Yet another aspect of the present invention relates to the use of one or more of the aforementioned flavour modulating substances for improving the flavour of foodstuffs, beverages, orally administered pharmaceuticals, tobacco products or oral care products.

Typical examples of foodstuffs according to the present invention include yoghurt, ice cream, desserts, confectioneries, bakery products, sweet snacks, savoury snacks, seasonings, sauces, stock, soups, dressings and ready meals. The benefits of the present invention may also be realised in beverages, in oral care products such as toothpaste and mouthwash, in orally administered pharmaceuticals such as pills and elixirs and in tobacco products, which includes any type of tobacco product for smoking as well as for non-smoking applications. It is noted that tobacco-like products are available for both smoking and non-smoking applications. The use of the present flavour modulating substances in these tobacco substitutes is also encompassed by the present invention.

Yet another aspect of the present invention relates to a product selected from the group consisting of foodstuffs, beverages, orally administered pharmaceuticals, tobacco products and oral care products, said product comprising at least 0.01 ppm, preferably between 0.1 and 10,000 ppm (mg/kg) of one or more flavour modulating substances as defined herein before. More preferably, the product contains at least 1 ppm, most preferably at least 5 ppm of the one or more flavour modulating substances. Typically, the aforementioned products contain the flavour modulating substance(s) in a concentration of not more than 5,000 ppm, preferably of not more than 2,000 ppm. The present products may further comprise one or more other flavouring substances, typically in amounts of 5-20,000 ppm, more preferably 10-10,000 ppm. The precise level in which the present substances are incorporated depends on the nature of the flavour modulating substance(s) and the nature of the product, as will be clear to the skilled person. In a particularly preferred embodiment of the invention, said product is selected from the group of foodstuffs, beverages, tobacco products and oral care products, most preferably from the group of foodstuffs and beverages.

Yet another aspect the present invention relates to a process of improving the flavour of a foodstuff, a beverage, an orally administered pharmaceutical product, a tobacco product or an oral care product, comprising adding to said product one or more flavour modulating substances as defined herein before. More preferably the present process comprises adding to said product an amount of at least 0.01 ppm (mg/kg), more preferably at least 0.1 ppm, still more preferably at least 5 ppm, most preferably at least 10 ppm of the present one or more flavour modulating substances. It is furthermore preferred that said amount does not exceed 10,000 ppm (mg/kg), more preferably it does not exceed 5,000 ppm, most preferably it does not exceed 2,000 ppm.

A further aspect of the invention relates to flavour modulating substances as defined herein before, with the additional proviso that if one of $R^1$ and $R^2$ represents a hydroxyl group, the other one does not represent the residue of tyrosine, phenylalanine or arginine.

The present flavour modulating substances are suitably prepared from commercially available products. Typically the starting materials comprise a dicarboxylate selected from dicarboxylic acid represented by the following formula (II) and/or salts, esters and or anhydrides thereof:

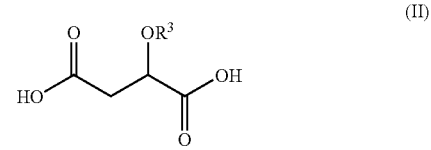

(II)

wherein $R^3$ has the same meaning as defined herein before in relation to formula (I) as well as a primary amine selected from the group of proteogenic or non-proteogenic amino acids; peptides; and substances represented by the formula $NH_2-X$ and salts thereof, wherein X has the same meaning as defined herein before. Thus, another aspect of the invention relates to a process of preparing flavour modulating substances, comprising reacting a dicarboxylate as defined herein before with a primary amine as defined herein before.

The present method of preparing flavour modulating substances comprises processes that make use of conventional reactions. Preferably said reaction is performed by heating to reflux said reactants in an organic solvent, such as toluene, for a period of between 0.1-10 hours. According to a preferred embodiment, the reactants are used in a molar ratio of between 1:1 and 1:10.

According to the present processes the reaction products are typically obtained as a precipitate and can be isolated by evaporating the solvent and optionally further purified using any of the techniques known by the skilled person, such as chromatography and crystallization.

In a preferred embodiment certain hydroxyl-, amino- and/or carboxyl groups of the starting materials may be protected in order to increase the yield of flavour modulating substances according to the present invention, when carrying out the present processes. It will be clear to the skilled person how to prepare these protected starting materials.

Typically, the aforementioned process is carried out by first preparing a mixture of the dicarboxylate and primary amine; followed by heating said mixture. In a preferred embodiment, the mixture contains at least 10 wt %, preferably at least 20 wt % and most preferably at least 30 wt % of the dicarboxylate. The primary amines are typically present in the mixture in a concentration of at least 0.5 wt %, more preferably 1.0 wt %, preferably of at least 5.0 wt. %.

The present invention, in another embodiment, encompasses flavour modulating compositions obtainable by the processes described above, flavouring compositions comprising these and the use thereof for modulating the flavour of foodstuffs, beverages, pharmaceutics or oral care products.

According to a particularly preferred embodiment of the present process, the reaction of dicarboxylate and the primary amine is carried out in the presence of a carbohydrate source. Typically, the reaction is carried out by first preparing a mixture of (i) dicarboxylate; (ii) the primary amine; and the carbohydrate source, followed by heating said mixture.

In a particularly preferred embodiment of the present process a Maillard flavour preparation, preferably a process flavour, is produced by heating a mixture of (i) a carbohydrate source; (ii) a nitrogen source, said nitrogen source comprising 0.5-100 wt %, preferably 5-100 wt %, most preferably 10-100 wt %, of the primary amine, and (iii) the dicarboxylate.

The combination of nitrogen source and carbohydrate source preferably represents at least 1.0 wt % of the mixture before it is heated. More preferably, said mixture represents at least 5.0 wt % of the mixture. Maillard flavour preparations obtained by said process will typically comprise one or more of the present flavour modulating substances. Thus, the aforementioned process preferably yields a Maillard flavour preparation comprising 0.0001-0.01 wt %, preferably 0.0001-0.001 wt % of one or more substances according to formula (I).

The term "Maillard flavour preparation" as used herein refers to a flavour preparation which is obtained by heating a mixture of ingredients including a nitrogen source, preferably amino nitrogen, and a carbohydrate source, preferably a reducing sugar. The terms "process flavour" or "reaction flavour" which are used interchangeably herein refer to compositions or products obtained by heat processing together a protein nitrogen source and a carbohydrate source, at a temperature, preferably, not exceeding 180° C. In the present process it is particularly preferred to heat the combination of carbohydrate source, nitrogen source and liquid phase to a temperature of between 60-180° C., even more preferably between 100-140° C. According to a preferred embodiment the heating is carried out for a period of 0.1-8 hours, preferably of 0.5-7 hours.

According to a particularly preferred embodiment the dicarboxylates are present in the mixture as a continuous liquid phase. The term "liquid" as used herein in relation to the continuous liquid phase refers to the fact that, especially under the heating conditions employed, the continuous phase exhibits fluid or flowing behaviour. Furthermore, it should be understood that the term liquid embraces emulsions and suspensions.

According to a preferred embodiment of the present invention the process is performed in a continuous liquid phase containing at least 40 wt %, more preferably at least 45 wt %, most preferably at least 50 wt % of the dicarboxylate. The present continuous liquid phase advantageously comprises water in an amount sufficient to liquefy the dicarboxylate, e.g. in an amount of at least 2 wt. %, even more preferably at least 5 wt. %. It is preferred that the amount of water does not exceed 70 wt. %, based on the total weight of the continuous liquid phase, preferably it does not exceed 60 wt. %, more preferably it does not exceed 45 wt. %.

The carbohydrate source can be any type conventionally used in the field of process flavours and Maillard flavour preparations. Preferably the carbohydrate source comprises a reducing sugar. Non-limiting examples include ribose, xylose, glucose, fructose, rhamnose, lactose, maltose and sucrose.

The present "nitrogen source", besides the primary amines may furthermore comprise a protein nitrogen source, autolyzed yeasts, peptides, amino acids and/or their salts, decarboxylated amino acids, nucleosides, nucleotides, salts thereof and mixtures thereof.

In a preferred embodiment of the present process the nitrogen source and the carbohydrate source are employed in a weight ratio within the range of 1:20 to 20:1. In another preferred embodiment the employed weight ratio of α-hydroxycarboxylate and/or α-hydroxycarboxylate derivative and/or salts thereof relative to the combination of carbohydrate source and nitrogen source is within the range of 1:1 to 20:1, more preferably within the range of 2:1 to 10:1.

The invention is further illustrated by means of the following examples

EXAMPLES

Example 1

Preparation of a Process Flavour 45 g of malic acid, 24 g of Yeast extract YEP LLS (Kerry bioscience) and 6 g dextrose were dissolved in 45 g water and reacted at 120° C. for 7 hours. 30 g of the reacted liquor was diluted with 90 g of water and the pH was adjusted to 6 with 50% NaOH solution. 60 g of maltodextrine (Dextrose equivalent 10) and 30 g of NaCl were then dissolved in the solution. The final liquid was spray-dried.

Example 2

Preparation of a Flavour Containing maloyl GMP 1 g GMP was mixed into to 8 g of glycerol. 2 g of malic acid were added to the mixture, which is then reacted at 120° C. for 1 hour. The reacted mixture is cooled to 70° C. and subsequently washed with 100 g IPA. The obtained residue was distilled to remove any IPA left and dissolved in 10 g water. The sample was stored at 4° C.

Example 3

Preparation of di-(2-hydroxy-ethyl)amide of malic acid 32.5 gram diethyl malate (0.21 mol) and 26.3 gram ethanolamine (0.42 mol) were stirred and heated to 120° C. while distilling off ethanol. 15 ml ethanol was removed by distillation and a residual light yellow solid was obtained. After 2 hours, the mixture was cooled to room temperature and 100 ml ethyl acetate was added and stirred. The mixture was then filtered under vacuum. The light yellow powder was washed with ethyl acetate, and dried in the vacuum oven. NMR-analysis showed that the sample contained over 95% of the_di-(2-hydroxy-ethyl)amide of malic acid.

Example 4

Preparation of N-Maloyl-Methionine

Step 1: Preparation of the Imide of Acetoxysuccinic Anhydride and Methionine

A 250 ml reaction flask was equipped with a thermometer, stirrer, refluxcondensor with a Dean Stark and nitrogen inlet. An amount of 0.05 mol (7.9 g) of (S)-(−)-2-acetoxysuccinic acid anhydride and 0.05 mol (7.46 g) of methionine were stirred thoroughly in 150 ml of toluene. The mixture was heated till reflux during 8 hours under a slow nitrogen flow. The mixture was allowed to cool to room temperature and left to stand overnight. A very sticky residue (product 1) was formed at the bottom of the reaction flask. The toluene was decanted and evaporated using a rotavapor ($T_{bath}$=60° C., p=15 mbar). A yellow sticky residue (product 2) was obtained. The NMR spectrum of the product was not in contradiction to the desired product.

Step 2: Preparation of N-Maloyl-Methionine 7.3 g of the residue of the toluene fraction was dissolved in 60 ml of 2.55 M KOH and stirred at room temperature for 8 hours under a nitrogen flow. The colour changed to orange/purple. Then the water was removed with using a rotavapor. The obtained white/yellow solid was solved in 20 ml of water and the pH was adjusted to 2 by adding concentrated HCl. The water was removed using a rotavapor ($T_{bath}$=60° C., p=15 mbar). The obtained residue was extracted with 75 ml of boiling acetonitril. After filtration of the mixture, a white powdery residue was obtained. The acetonitril solution was evaporated. A yellow sticky oil was obtained.

The residue (product 1) was extracted again with cold ethanol. After evaporation of the ethanol, 2 g of a glassy oil was gained. The presence of maloyl methionine was confirmed by NMR but the product was also shown to contain still 20% of methionine. For further purification, preparative liquid chromatography was used. A Gilson (Villiers le Bel, France) pump model 321 with a liquidhandler model 215 was used equipped with an ELDS detector. The separation was carried out on one 100×20 mm ID 5 μm Atlantis dC 18 columns (Waters, Milford, Mass., USA). Gradient elution was carried out with Milli-Q water with 1% formic acid (A) and methanol (pro analysis) (B) (Merck, Darmstadt, Germany) as follows: 0-5 min 83% A, 5-7.5 min linear gradient to 33% B, 7.5-8.5 min linear gradient to 100% B, 8.5-13 min 100% B, 13-14 min linear gradient back to 83% A (initial conditions), 14-18 min 80% A (re-equilibration) (%, v/v). The flow rate was 10 ml/min.

1 g of the glassy oil obtained previously was dissolved in 100 ml of water and 2 ml of this solution was injected. Fraction 1 was collected, concentrated with a rotavapor to remove the solvent and the presence of N lactoyl methionine was confirmed by NMR analysis. Fraction 1 was concentrated with a rotavapor to remove the solvent and diluted in water to a final volume of 200 ml. 100 g of maltodextrin (MD 10) was dissolved in the solution and the whole was spray-dried.

Example 5

Preparation of A Mixture of the 2-OH And 3-OH N-(2-hydroxyethyl) Succinic Mono Amide An amount of 2.4 g of ethanolamine (37.5 mmol) was dissolved in 15 ml of water. An amount of 6.0 g of 2-acetoxysuccinic anhydride (37.5 mmol) was added in 2 hours. The reaction mixture was stirred for 24 hours at room temperature, the pH was kept at 9-9.5 with concentrated NaOH solution. The water was evaporated and 15 ml water was added. Then ion exchanger Dowex 50WX8 was added until the pH was 2. The mixture was stirred overnight. The mixture was filtered and evaporated. The residue was analysed by NMR and contained 70% of the desired compounds (a mixture of the 2-OH and 3-OH N-(2-hydroxyethyl) succinic mono amide).

Example 6

Two samples were prepared:
Sample A: 0.6% NaCl and 0.03% mono sodium glutamate
Sample B: 0.6% NaCl, 0.03% mono sodium glutamate and 0.01% of the_di-(2-hydroxy-ethyl)amide of malic acid as prepared in example 3

Both samples were evaluated by a professional panel and described as follows:
Sample A: "salty" "umami", "brothy"
Sample B: "high impact", "salty" "umami", "brothy", "meaty", "salivating", "long lasting"

Example 7

The following powder flavours were prepared:
A: 1.6 g of NaCl
  0.44 g of mono sodium glutamate
  1.6 g of flavour type Cheese Gouda
B: 1.6 g of NaCl
  0.44 g of mono sodium glutamate
  1.6 g of flavour type Cheese Gouda
  1.6 g of flavour as prepared in example 1
C: 1.6 g of NaCl
  0.44 g of mono sodium glutamate
  1.6 g of flavour type Cheese Gouda
  1 g of maloyl methionine as prepared in example 4

The flavours were applied at a 6% dosage on potato crisps. The crisps were then evaluated by a professional panel and described as follow:
A: Salty, umami, cheesy
B: Salty, umamy, very cheesy, body, full, cheese aftertaste, authentic cheesy profile
C: Salty, umamy, very cheesy, body, full, cheese aftertaste, dairy, fatty, authentic cheesy profile

Example 8

Two samples were prepared:
Sample A: 0.6% NaCl and 0.03% mono sodium glutamate
Sample B: 0.6% NaCl, 0.03% mono sodium glutamate and 0.002% of mono N-(2-hydroxyethyl)amide of malic acid as prepared in example 5.

Both samples were evaluated by a professional panel and described as follows:
Sample A: "salty" "umami", "brothy"
Sample B: "high impact", "salty" "umami", "very brothy", "meaty", "salivating", "long lasting"

The invention claimed is:
1. A flavour composition comprising at least 0.1 wt. % of one or more flavouring substances and between 0.001 and 95 wt. % of one or more flavour modulating substances represented by formula (I), edible salts thereof and edible esters thereof:

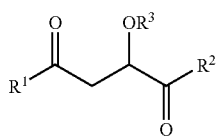

(I)

wherein:

R¹ and R² independently represent:
- a hydroxyl group;
- an amino acid residue;
- the residue of a peptide; or
- a moiety represented by the formula —NH—X, wherein X represents:
  1) C1-C4 alkyl or C4-C7 aralkyl, each substituted with a substituent selected from hydroxyl or C1-C3 alkoxyl, and each optionally further substituted with one or more substituents selected from hydroxyl, oxo, C1-C3 alkoxyl and C1-C3 alkyl;
  2) a purine or pyrimidine radical, each optionally substituted with one or more substituents selected from the group of amino, oxo, methyl and monosaccharide units, said monosaccharide unit optionally being esterified with a mono-, di- or triphosphate group; or
  3) C5-C7 polyhydroxy carboxylic acid or an intramolecular-condensation product thereof; or
  4) C5-C7 polyhydroxy carbonyl or an intramolecular-condensation product thereof;

and wherein R³ represents hydrogen or C1-C3 alkyl; with the proviso that if one of R¹ and R² represents a hydroxyl group, the other one does not represent a hydroxyl group or the residue of tyrosine.

2. The flavour composition according to claim 1, wherein R¹ and R² independently represent a hydroxyl group or said moiety is represented by the formula —NH—X.

3. The flavour composition according to claim 1, wherein R¹ and R² independently represent a hydroxyl group; or a moiety represented by the formula —NH—X, wherein X represents C2-C3 alkyl substituted with one hydroxyl group and optionally 1 or 2 substituents selected from hydroxyl and methyl; a purine or pyrimidine radical, each at least substituted with a monosaccharide unit, which is esterified with a mono-, di- or triphosphate group; phenylmethyl or phenylethyl, wherein the phenyl ring is substituted with 1-3 substituents selected from hydroxyl, methoxyl and ethoxyl; C5-C7 polyhydroxy carbonyl or an intramolecular condensation product thereof; or C5-C7 polyhydroxy carboxylic acid or an intramolecular condensation product thereof.

4. The flavour composition according to claim 1, wherein R¹ and R² independently represent a hydroxyl group; the residue of guanosine monophosphate (GMP), adenosine monophosphate (AMP) or cytidine monophosphate (CMP); the residue of ethanolamine, 2-amino-1,3-propanediol, 3-amino-1,2-propanediol, 3-amino-1-propanol, 2-amino-1,3-propanediol, 1-amino-2-propanol, 2-amino-1-propanol, 1-amino-2-methyl-2-propanol or 2-amino-2-methylpropanol; the residue of tyramine, vanillylamine, 4-hydroxybenzylamine or dopamine; the residue of a 2-deoxy-2-amino aldose; or the residue of a 2-deoxy-2-amino aldonic acid.

5. Flavour composition according to claim 1, wherein R³ is hydrogen.

6. A product for oral consumption comprising between 0.1 and 10,000 ppm (mg/kg) of one or more flavour modulating substances represented by formula (I), edible salts thereof and edible esters thereof:

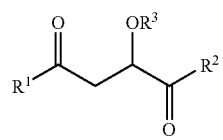

(I)

wherein R¹ and R² independently represent:
- a hydroxyl group;
- an amino acid residue;
- the residue of a peptide; or
- a moiety represented by the formula —NH—X, wherein X represents:
  1) C1-C4 alkyl or C4-C7 aralkyl, each substituted with a substituent selected from hydroxyl or C1-C3 alkoxyl, and each optionally further substituted with one or more substituents selected from hydroxyl, oxo, C1-C3 alkoxyl and C1-C3 alkyl;
  2) a purine or pyrimidine radical, each optionally substituted with one or more substituents selected from the group of amino, oxo, methyl and monosaccharide units, said monosaccharide unit optionally being esterified with a mono-, di- or triphosphate group; or
  3) C5-C7 polyhydroxy carboxylic acid or an intramolecular-condensation product thereof; or
  4) C5-C7 polyhydroxy carbonyl or an intramolecular-condensation product thereof;

and wherein R³ represents hydrogen or C1-C3 alkyl; with the proviso that if one of R¹ and R² represents a hydroxyl group, the other one does not represent a hydroxyl group or the residue of tyrosine.

7. The product according to claim 6, wherein the product is a foodstuff, beverage, pharmaceutical, tobacco product, or oral care products.

8. A method of flavouring a product comprising incorporating into the product between 0.1 and 10,000 ppm (mg/kg) of one or more flavour modulating substances represented by formula (I), edible salts thereof and edible esters thereof:

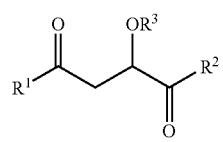

(I)

wherein:

R¹ and R² independently represent:
- a hydroxyl group;
- an amino acid residue;
- the residue of a peptide; or
- a moiety represented by the formula —NH—X, wherein X represents:
  1) C1-C4 alkyl or C4-C7 aralkyl, each substituted with a substituent selected from hydroxyl or C1-C3 alkoxyl, and each optionally further substituted with one or more substituents selected from hydroxyl, oxo, C1-C3 alkoxyl and C1-C3 alkyl;
  2) a purine or pyrimidine radical, each optionally substituted with one or more substituents selected from the group of amino, oxo, methyl and monosaccharide units, said monosaccharide unit optionally being esterified with a mono-, di- or triphosphate group; or 3) C5-C7 polyhydroxy carboxylic acid or an intramolecular-condensation product thereof; or 4) C5-C7 polyhydroxy carbonyl or an intramolecular-condensation product thereof;

and wherein $R^3$ represents hydrogen or C1-C3 alkyl; with the proviso that if one of $R^1$ and $R^2$ represents a hydroxyl group, the other one does not represent a hydroxyl group or the residue of tyrosine.

9. A flavour modulating substance represented by formula (I), edible esters thereof and edible salts thereof:

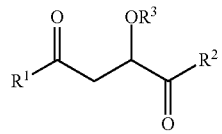

wherein:

$R^1$ and $R^2$ independently represent:

a hydroxyl group;

an amino acid residue;

the residue of a peptide; or a moiety represented by the formula —NH—X, wherein X represents:

1) C1-C4 alkyl or C4-C7 aralkyl, each substituted with a substituent selected from hydroxyl or C1-C3 alkoxyl, and each optionally further substituted with one or more substituents selected from hydroxyl, oxo, C1-C3 alkoxyl and C1-C3 alkyl;

2) a purine or pyrimidine radical, each optionally substituted with one or more substituents selected from the group of amino, oxo, methyl and monosaccharide units, said monosaccharide unit optionally being esterified with a mono-, di- or triphosphate group; or 3) C5-C7 polyhydroxy carboxylic acid or an intramolecular-condensation product thereof; or 4) C5-C7 polyhydroxy carbonyl or an intramolecular-condensation product thereof;

and wherein $R^3$ represents hydrogen or C1-C3 alkyl;

with the proviso that if one of $R^1$ and $R^2$ represents a hydroxyl group, the other one does not represent a hydroxyl group or the residue of tyrosine, phenylalanine or arginine.

10. The flavour modulating substance according to claim 9, wherein $R^1$ and $R^2$ independently represent a hydroxyl group; the residue of guanosine monophosphate (GMP), adenosine monophosphate (AMP) or cytidine monophosphate (CMP); the residue of ethanolamine, 2-amino-1,3-propanediol, 3-amino-1,2-propanediol, 3-amino-1-propanol, 2-amino-1,3-propanediol, 1-amino-2-propanol, 2-amino-1-propanol, 1-amino-2-methyl-2-propanol or 2-amino-2-methylpropanol; the residue of tyramine, vanillylamine, 4-hydroxybenzylamine or dopamine; the residue of a 2-deoxy-2-amino aldose; or the residue of a 2-deoxy-2-amino aldonic acid.

11. A process of preparing flavour modulating substances, comprising reacting a dicarboxylate selected from dicarboxylic acid of formula (II) and/or salts, esters and/or anhydrides thereof:

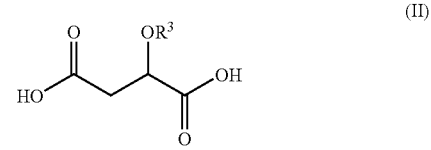

wherein $R^3$ is:

a primary amine selected from the group consisting of proteogenic or non-proteogenic amino acids, peptides, and substances represented by the formula NH2-X and salts thereof; or C1-C3 alkyl, wherein X represents:

1) C1-C4 alkyl or C4-C7 aralkyl, each substituted with a substituent selected from hydroxyl or C1-C3 alkoxyl, and each optionally further substituted with one or more substituents selected from hydroxyl, oxo, C1-C3 alkoxyl and C1-C3 alkyl;

2) a purine or pyrimidine radical, each optionally substituted with one or more substituents selected from the group of amino, oxo, methyl and monosaccharide units, said monosaccharide unit optionally being esterified with a mono-, di- or triphosphate group; or 3) C5-C7 polyhydroxy carboxylic acid or an intramolecular-condensation product thereof; or 4) C5-C7 polyhydroxy carbonyl or an intramolecular-condensation product thereof.

* * * * *